(12) United States Patent
Ramirez

(10) Patent No.: US 9,707,165 B2
(45) Date of Patent: *Jul. 18, 2017

(54) UV PROTECTIVE SKIN TREATMENT COMPOSITIONS AND SCREENING METHODS

(71) Applicant: JR Chem LLC, Fort Lauderdale, FL (US)

(72) Inventor: Jose E. Ramirez, Fort Lauderdale, FL (US)

(73) Assignee: JR Chem, LLC, Fort Lauderdale, FL (US)

( * ) Notice: Subject to any disclaimer, the term of this patent is extended or adjusted under 35 U.S.C. 154(b) by 24 days.

This patent is subject to a terminal disclaimer.

(21) Appl. No.: 14/818,692

(22) Filed: Aug. 5, 2015

(65) Prior Publication Data

US 2015/0335559 A1 Nov. 26, 2015

Related U.S. Application Data

(62) Division of application No. 13/544,206, filed on Jul. 9, 2012, now Pat. No. 9,116,112.

(60) Provisional application No. 61/506,394, filed on Jul. 11, 2011.

(51) Int. Cl.

| | | |
|---|---|---|
| *A61K 31/40* | (2006.01) | |
| *A61K 8/34* | (2006.01) | |
| *A61K 8/49* | (2006.01) | |
| *A61Q 17/04* | (2006.01) | |
| *A61Q 19/00* | (2006.01) | |
| *A61Q 19/02* | (2006.01) | |
| *A61K 8/60* | (2006.01) | |
| *A61K 8/69* | (2006.01) | |
| *G01N 27/26* | (2006.01) | |

(52) U.S. Cl.
CPC ............ *A61K 8/4913* (2013.01); *A61K 8/347* (2013.01); *A61K 8/498* (2013.01); *A61K 8/4953* (2013.01); *A61K 8/602* (2013.01); *A61K 8/69* (2013.01); *A61K 31/40* (2013.01); *A61Q 17/04* (2013.01); *A61Q 19/00* (2013.01); *A61Q 19/001* (2013.01); *A61Q 19/02* (2013.01); *G01N 27/26* (2013.01); *A61K 2800/522* (2013.01); *A61K 2800/592* (2013.01)

(58) Field of Classification Search
None
See application file for complete search history.

(56) References Cited

U.S. PATENT DOCUMENTS

| | | | | |
|---|---|---|---|---|
| 6,383,471 B1 * | 5/2002 | Chen | .................... | A61K 9/1075 424/401 |
| 2004/0146539 A1 | 7/2004 | Gupta | | |
| 2004/0166069 A1 | 8/2004 | Gupta | | |
| 2005/0008665 A1 * | 1/2005 | Batzer | ..................... | A61K 8/355 424/401 |
| 2005/0276762 A1 | 12/2005 | Das et al. | | |
| 2006/0246019 A1 | 11/2006 | Cole et al. | | |
| 2006/0246020 A1 | 11/2006 | Cole et al. | | |
| 2009/0155371 A1 | 6/2009 | Sojka et al. | | |
| 2009/0189090 A1 | 7/2009 | Meyer et al. | | |
| 2011/0165092 A1 * | 7/2011 | Cau | .......................... | A61K 8/55 424/43 |
| 2015/0335561 A1 * | 11/2015 | Ramirez | ................ | A61K 8/347 424/60 |

FOREIGN PATENT DOCUMENTS

| | | | | |
|---|---|---|---|---|
| EP | 1078638 | 2/2001 | | |
| EP | 1136064 | 9/2001 | | |
| FR | WO 2009112653 A2 * | 9/2009 | ............... | A61K 8/55 |
| WO | 2005105925 | 10/2005 | | |
| WO | 2007128723 | 11/2007 | | |
| WO | 2009015372 | 1/2009 | | |
| WO | 2010019413 | 2/2010 | | |

OTHER PUBLICATIONS

International Search Report, International Application No. PCT/US2014/046032, dated Nov. 11, 2012, (1 page).
Cecchi, et al. "The First Quantitative Rating System of the Antioxidant Capacity of Beauty Creams via the Briggs-Rauscher Reaction; A Crucial Step Towards Evidence-Based Cosmetics", Dec. 2010. Analyst, vol. 136, Issue 3, pp. 613-618.
Petit, et al. "Skin-Lightening Products Revisited". Blackwell Publishing, LTD, Internation Journal of Cosmetic Science, 2001, vol. 25, pp. 169-181.

* cited by examiner

*Primary Examiner* — Abigail Fisher
(74) *Attorney, Agent, or Firm* — Perman & Green, LLP

(57) ABSTRACT

Provided are methods of screening antioxidants for skin protective capacity and antioxidant formulations which protect the skin from UV radiation. The method of screening antioxidants for protecting the skin from UV radiation includes using the Briggs-Rauscher Oxidant Method (BROM) method to one or more antioxidants for predicting protection to the epidermal layer. One advantageous antioxidant formulation for use in sun screens, lip balms and other types of topically applied skin care products for protecting the skin from UV radiation includes a mixture of antioxidants in the skin care product including an effective amount of arbutin in combination with BHT, wherein the ratio of arbutin to BHT in the skin care product ranges from 1:4 to 4:1, and wherein the measured BROM value of the antioxidant mixture is greater than the sum of the BROM values of the individual antioxidants in the mixture at the same concentration. The measured BROM value of the resultant product is greater than or equal to 0.2 sec/µg. The antioxidant formulation may also optionally include hydroquinone, resveratrol, uric acid and/or atorvastatin.

8 Claims, 7 Drawing Sheets

UV PROTECTIVE SKIN TREATMENT COMPOSITIONS AND SCREENING METHODS

CROSS-REFERENCE TO RELATED APPLICATIONS

This application is a divisional application of U.S. patent application Ser. No. 13/544,206, filed on Jul. 9, 2012, and claims the benefit of U.S. Provisional Patent Application No. 61/506,394, filed on Jul. 11, 2011. The disclosures of which are incorporated herein by reference in their entireties.

FIELD

The present disclosure relates to the field of antioxidant compositions for protection against cellular damage to the layers of the skin from free radicals generated from sunlight exposure or during metabolic processes in the human body. It also relates to novel uses of screening methods for evaluating antioxidants for their protective capacity to the different layers of the skin. More particularly, the present disclosure relates to novel combinations of antioxidants that have enhanced antioxidant capacity as measured by the Briggs-Rauscher Oscillation Reaction Method (BROM) and the use of such antioxidants in pharmaceutical or dermatological carrier compositions for enhanced antioxidant capacity.

BACKGROUND

The skin of the human body is an organ that acts as a protective interface with the ambient environment. The epidermis is the outermost layer of the skin. It forms a waterproof, protectivewrap over the body's and lips' surfaces and is made up of stratified squamous epithelium which is an underlying basal lamina. The epidermis contains no blood vessels, and cells in the deepest layer obtain nutrients by diffusion from the blood capillaries extending to the upper layers of the dermis. The main type of cells which comprise the epidermis are Merkel cells, keratinocytes with melanocytes and Langerhans cells. The epidermis can be further subdivided into the following strata (beginning with the outermost layer): corneum, lucidum (only in palms of hands and bottoms of feet), granulosum, spinosum, and basale. Cells are formed through mitosis at the basal layer. The daughter cells move up the strata by changing shape and composition as they die due to isolation from their blood source. The cytoplasm is released and protein keratin is inserted. The cells move up to the corneum and slough off through desquamation, which is a process called keratinization taking place over a 27-day period. This keratinized layer of skin and lips is responsible for keeping water in the body and keeping other harmful chemicals and pathogens out while providing a natural barrier to infection. The external layers of the skin change in the number of cellular layers, and while, for example, the facial skin has sixteen cellular layers, the specialized keratinized outer mucosa of the lips only has three to five cellular layers. Always the common factor is that the outer cellular layers are very low in water (circa 20%), while the deeper layers have a much higher water content (circa 80%).

The skin is exposed to several forms of stress including ozone, ultraviolet (UV) radiation, air pollution, pathologic microorganisms, chemical oxidants and topically applied substances. Oxidative stress occurs when some molecules (oxidizing agents) take electrons from the other molecules or atoms. The substances that can exist with missing electrons are called free radicals. Most of these free radicals are oxygen molecules or atoms. Free radicals are highly reactive in that they are ready to give away an electron or to accept one. After the lonesome electron pairs, the atom loses its radical activity, but the atom that has just lost an electron becomes a free radical in turn. These free radical reactions are a necessary part of metabolic processes, however, too many free radicals cause dangerous chain reactions that may destroy cellular composition and may cause damage to DNA, skin proteins and lipids (fats) through these oxidative stresses. The skin of the human body is exposed to oxidative stressors through the environment, bi-products of metabolism, and lifestyle factors such as smoking, alcohol, and UV radiation exposure. These oxidative stresses stimulate the production of unstable molecules otherwise known as reactive oxygen species (ROS) or free radicals. Free radicals are highly reactive molecules that are created as bi-products of normal metabolism (intrinsic) and environmental stressors (extrinsic), and are responsible for cellular damage to the skin. Cellular damage to the layers of the skin can be from free radicals generated from sun light exposure or during metabolic processes in the human body.

Sunlight in a broad sense refers to the total frequency spectrum of electromagnetic radiation given off by the sun. The solar spectrum consists of electromagnetic radiation with a wavelength ranging from 200 to 2500 nm, which includes UV, visible and infrared radiation. The UV portion of the spectrum (200 to 400 nm) is responsible for the most damage to human skin. The UV spectrum may be further broken down by the long wave portion (UVA), and a medium wave portion (UVB). Table 1 below provides a breakdown of the wavelength range and energy per photon for the UVA and UVB portions of the ultraviolet spectrum.

TABLE 1

| Name | Abbreviation | Wavelength range in nanometers | Energy per photon* |
| --- | --- | --- | --- |
| Ultraviolet A, long wave, or black light | UVA | 400 nm-315 nm | 3.10-3.94 eV |
| Ultraviolet B or medium wave | UVB | 315 nm-280 nm | 3.94-4.43 eV |

*1 eV = $1.6 \times 10^{-19}$ joule

The UV flux at the Earth's surface has been determined and the erythemal dose to human skin at local noon has been calculated for all latitudes and it varies from 0.0 to 0.4 W/m$^2$. Because of variations in the intensity of UV radiation passing through the atmosphere, the risk of sunburn increases with proximity to the tropic latitudes, located between 23.5° north and south latitude. The noon erythemal dose to human skin at 23.5° latitude is 0.25 W/m$^2$. FIG. 1 shows the depth of penetration for UVA and UVB radiation through the skin. From FIG. 1, it can be seen that the sun burning radiation (wavelengths shorter than 315 nanometers) is nearly all absorbed in the epidermis, which is where UVB radiation has it most harmful effects. Wavelengths longer than 315 nanometers (UVA) is nearly all absorbed in the epidermis and dermis, which is where UVA radiation has it most harmful effects.

Upon absorption of UV radiation energy by photo reactive molecules (chromophore), a photo chemical reaction is induced. The absorption of the radiation energy by the chromophores (P) in its ground state will occur. The formation of the excited (usually triplet) state ($^3$P) molecule occurs. The excited state molecules then participate in oxygen dependent processes (i.e., photodynamic processes) in two major pathways: Type I or Type II reactions, both of which result in cytotoxic injury to the skin. The cytotoxic injury by the UV radiation causes mutations and death in cells of the skin. The Type I reaction involves transfer of an electron or a hydrogen atom to the excited state photosensitizer ($^3P$) resulting in the formation of free radicals (Equation 1 below), which leads to oxidative reduction reactions that results in hydrogen peroxide formation and subsequent cell damage (Equations 2 and 3 below).

$$^3P + RH \rightarrow PH. + R. \quad (1)$$

$$PH. + PH. \rightarrow P + PH_2 \quad (2)$$

$$PH_2 + O_2 \rightarrow P + H_2O_2 \quad (3)$$

$$^3P + O_2 \rightarrow P + {}^1O_2 \quad (4)$$

The interaction of $^3P$ with ground state oxygen could result in the formation of superoxide anions $(O_2.)-$, which in turn, can be converted into highly reactive and cytoxic hydroxyl radicals (OH.). The Type II reaction depicted above is also known as an energy transfer process. Transfer of energy to ground state oxygen results in the formation of singlet oxygen ($^1O_2$), which is highly reactive and has a lifetime of 50 nanoseconds (See equation 4 above). Cytotoxic injury occurs upon singlet oxygen-induced oxidation of amino acids and unsaturated fatty acids with interaction of the latter resulting in the formation of hydroperoxides, which initiate lipid and protein oxidation.

Exposure to the UV spectrum of sunlight through the mechanisms described above has been associated with skin cancer. Excessive UV radiation from sun exposure causes DNA damage, inflammation, erythema, sunburn, immunosuppression, photoaging, gene mutations, and skin cancer. Sunburn can also be caused by pharmaceutical products that sensitize some users to UV radiation. Certain antibiotics, oral contraceptives, and tranquilizers have this effect. In general, people with fair hair and/or also freckles have a greater risk of sunburn than others because of their lighter skin tone and low melanin in the skin. Upon DNA damage, tumor suppressor protein undergoes phosphorylation and translocation to the nucleus and aids in DNA repair or causes apoptosis. Excessive UV exposure overwhelms DNA repair mechanisms. UV radiation is a common cause of melanoma and sunburn. Sunburn is caused by direct DNA-damage, whereas melanoma is caused by indirect DNA-damage. Protecting against sunburn does not necessarily protect against melanoma, however protection of the skin from sunlight radiation is highly desirable. The preferred skin protection method against UV radiation damage is clothing, including hats. Moderate sun tanning without burning can also prevent subsequent sunburn, as it increases the amount of melanin, a skin photoprotectant pigment that is the skin's natural defense against overexposure. The erythemal diurnal dose rate for sun tanning is dependent on latitude and time of the solar day.

Sunscreens can help prevent sunburn, although they may not effectively protect against malignant melanoma, which either is caused by a different part of the UV spectrum or is not caused by sun exposure at all. Sunscreens utilize a combination of antioxidants, which are generally selected haphazardly without taking into consideration the physicochemical factors which will help prevent cytotoxic damage. The use of sunscreen is known to prevent the direct DNA damage that causes sunburn and the two most common forms of skin cancer, basal-cell carcinoma and squamous cell carcinoma. However, if sunscreen penetrates into the skin, it promotes indirect DNA damage, which causes the most lethal form of skin cancer, malignant melanoma. The existing SPF label value for sunscreen is based according to the formula SPF/Minimal Erythemal Dose 2/3 where the effective erythemal dose is 200 W/m². At a dose rate 0.250 W/m² it takes 800 seconds of local noon exposure at a latitude of 23° N (Key West, Fla.) to be exposed to 1 MED of UV radiation. In addition to UV mediated photosensitization, the sunscreen filter is absorbed into the skin, and prevents sunburn, but also increases the amount of free radicals, which in turn increases the risk for malignant melanoma. The harmful effect of photo-excited sunscreen filters on living tissue has been shown in many photobiological studies. Whether sunscreen prevents or promotes the development of melanoma depends on the relative importance of the protective effect from the topical sunscreen versus the harmful effects of the absorbed sunscreen. Therefore, it is highly desirable to develop compositions of antioxidants that will prevent UV induced oxidative damage to the outer layers of the skin.

In order to determine the various physiological effects of UV radiation on human skin, it is necessary to develop an understanding of the depth of penetration of the different UV wavelengths into the skin. But this is difficult because the skin is made up of optically inhomogeneous layers having different properties and varying in thickness and structure from one part of the body to another. An understanding of the different reaction mechanisms taking place with the skin from UV radiation and how the structure and chemical composition of skin varies from these UV induced oxidative stresses is important to developing skin treatment compositions that protect the skin from harmful UV radiation. Therefore, there is also a need to develop methods that aid in the screening and selection of antioxidant combinations that may be used to protect the skin from the harmful effects of UV radiation and other environmental and metabolic processes.

SUMMARY

According to the present disclosure, an advantageous method of screening antioxidants for protecting the outer layers of the skin from UV radiation includes the use of the Briggs-Rauscher Oxidant Method (hereinafter BROM) for predicting antioxidants for protection to the epidermal layers and to help minimize the damage caused by photodecomposition of exogenous materials that penetrate the surface of the skin while being applied for cosmetic or pharmaceutical purposes.

A further aspect of the present disclosure relates to advantageous antioxidant formulations for topically applied skin care products for protecting the skin from direct and indirect effects of UV radiation. The direct effects include the photodynamic processes previously described and the indirect effects include the phototoxicity generated by the photodecomposition of exogenous products present on the skin, e.g., treatment products, sunscreens and/or medicaments. A list of preferred antioxidants for this purpose are those that individually or in combinations, have sufficiently large BROM values to overcome free radical cellular photo damage induced by the radiative photon flux.

In one form of the present disclosure, an antioxidant formulation for use in sun screens, lip balms and other topically applied skin care products for protecting the skin from UV radiation includes: a mixture of antioxidants in the skin care product including an effective amount of arbutin and BHT, wherein the ratio of arbutin to BHT in the skin care product ranges from 1:4 to 4:1, and wherein the measured BROM value of the antioxidant mixture is greater than the sum of the BROM values of the individual antioxidants in the mixture at the same concentration.

In another form of the present disclosure, antioxidant formulation for use in sun screens, lip balms and other topically applied skin care products for protecting the skin from UV radiation includes: a mixture of antioxidants in the skin care product including an effective amount of atorvastatin and BHT, wherein the ratio of atorvastatin to BHT in the skin care product ranges from 1:2 to 1:1, and wherein the measured BROM value of the antioxidant mixture is greater than the sum of the BROM values of the individual antioxidants in the mixture at the same concentration.

In another form of the present disclosure, an antioxidant formulation for use in sun screens, lip balms and other topically applied skin care products for protecting the skin from UV radiation includes: a mixture of antioxidants in the skin care product including an effective amount of arbutin and hydroquinone, wherein the ratio of arbutin to hydroquinone in the skin care product ranges from 1:4 to 4:1, and wherein the measured BROM value of the antioxidant mixture is greater than the sum of the BROM values of the individual antioxidants in the mixture at the same concentration.

In another form of the present disclosure, an antioxidant formulation for use in sun screens, lip balms and other topically applied skin care products for protecting the skin from UV radiation includes: a mixture of antioxidants in the skin care product including an effective amount of hydroquinone and BHT, wherein the ratio of hydroquinone to BHT in the skin care product ranges from 1:4 to 4:1, and wherein the measured BROM value of the antioxidant mixture is greater than the sum of the BROM values of the individual antioxidants in the mixture at the same concentration.

In yet another form of the present disclosure, an antioxidant formulation for use in sun screens, lip balms and other topically applied skin care products for protecting the skin from UV radiation includes: a mixture of antioxidants in the skin care product including an effective amount of atorvastatin and uric acid, wherein the ratio of atorvastatin to uric acid in the skin care product ranges from 0.5:1 to 2:1, and wherein the measured BROM value of the antioxidant mixture is greater than the sum of the BROM values of the individual antioxidants in the mixture at the same concentration.

In yet another form of the present disclosure, an antioxidant formulation for use in sun screens, lip balms and other topically applied skin care products for protecting the skin from UV radiation includes: a mixture of antioxidants in the skin care product including an effective amount of uric acid, atorvastatin and BHT, wherein the ratio of uric acid, atorvastatin and BHT in the skin care product ranges from 1:1:4 to 4:1:1, and wherein the measured BROM value of the antioxidant mixture is greater than the sum of the BROM values of the individual antioxidants in the mixture at the same concentration.

In yet another form of the present disclosure, an antioxidant formulation for use in sun screens, lip balms and other topically applied skin care products for protecting the skin from UV radiation includes: a mixture of antioxidants in the skin care product including an effective amount of arbutin and resveratrol, wherein the ratio of arbutin to resveratrol in the skin care product ranges from 1:4 to 4:1, and wherein the measured BROM value of the antioxidant mixture is greater than the sum of the BROM values of the individual antioxidants in the mixture at the same concentration.

In still yet another form of the present disclosure, an antioxidant formulation for use in sun screens, lip balms and other topically applied skin care products for protecting the skin from UV radiation includes: a mixture of antioxidants in the skin care product including an effective amount of BHT and resveratrol, wherein the ratio of BHT to resveratrol in the skin care product ranges from 1:4 to 4:1, and wherein the measured BROM value of the antioxidant mixture is greater than the sum of the BROM values of the individual antioxidants in the mixture at the same concentration.

In still yet another form of the present disclosure, an antioxidant formulation for use in sun screens, lip balms and other topically applied skin care products for protecting the skin from UV radiation includes: a mixture of antioxidants in the skin care product including an effective amount of atorvastatin and hydroquinone, wherein the ratio of atorvastatin to hydroquinone in the skin care product ranges from 1:4 to 4:1, and wherein the measured BROM value of the antioxidant mixture is greater than the sum of the BROM values of the individual antioxidants in the mixture at the same concentration.

In still yet another form of the present disclosure, an antioxidant formulation for use in sun screens, lip balms and other topically applied skin care products for protecting the skin from UV radiation includes: a mixture of antioxidants in the skin care product including an effective amount of arbutin, hydroquinone and BHT, wherein the ratio of arbutin, hydroquinone and BHT in the skin care product ranges from 2:1:1 to 2:1:4, and wherein the measured BROM value of the antioxidant mixture is greater than the sum of the BROM values of the individual antioxidants in the mixture at the same concentration.

In still yet another form of the present disclosure, an antioxidant formulation for use in sun screens, lip balms and other topically applied skin care products for protecting the skin from UV radiation includes: a mixture of antioxidants in the skin care product including an effective amount of arbutin, BHT and resveratrol, wherein the ratio of arbutin, BHT and resveratrol in the skin care product ranges from 1:1:1 to 2:1:2, and wherein the measured BROM value of the antioxidant mixture is greater than the sum of the BROM values of the individual antioxidants in the mixture at the same concentration.

These and other features and attributes of the disclosed methods for screening skin protective antioxidants from UV radiation, and the antioxidant formulations for protecting the skin from UV radiation of the present disclosure will be apparent from the detailed description which follows, particularly when read in conjunction with the figures appended hereto.

BRIEF DESCRIPTION OF DRAWINGS

To assist those of ordinary skill in the relevant art in making and using the subject matter hereof, reference is made to the appended drawings, wherein.

DETAILED DESCRIPTION

Figure 1:
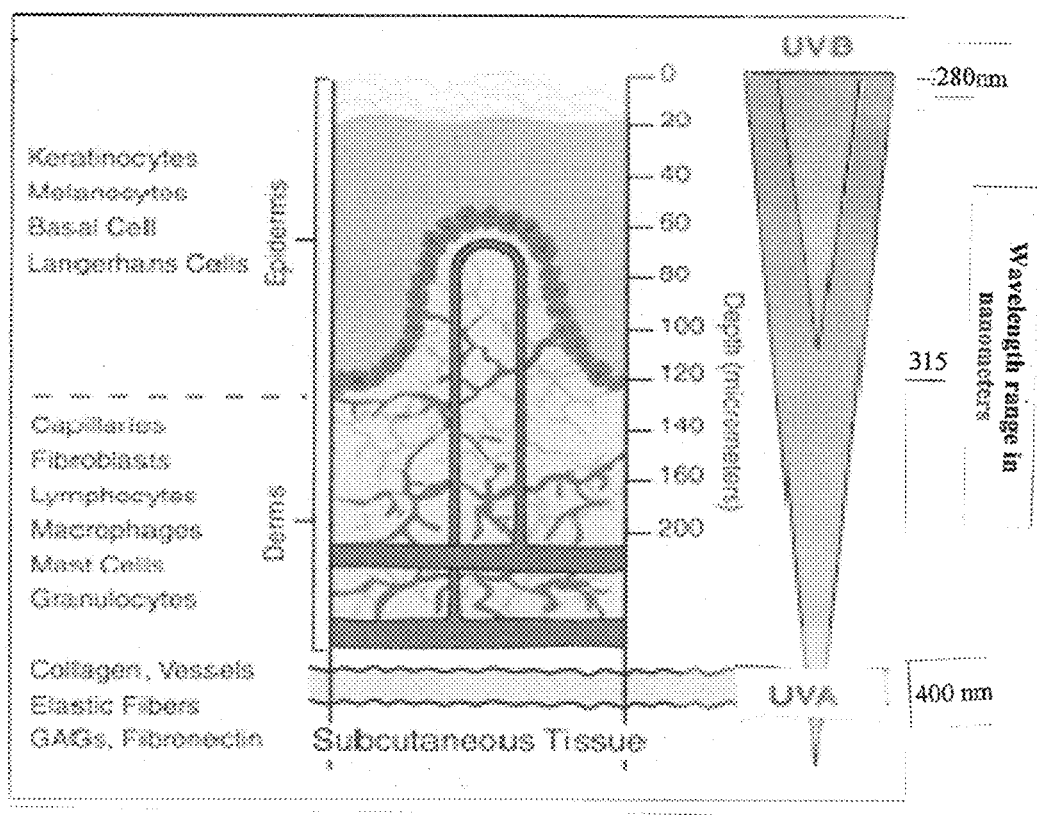
FIG. 1 depicts a schematic of the depth of penetration for UVA and UVB radiation through the epidermal and dermal layers of the skin.

The present disclosure provides novel methods for predicting the performance of antioxidants in sunscreens and other topically applied skin products and novel antioxidant combinations for use in such sunscreens and other topically applied skin products. All numerical values within the detailed description and the claims herein are modified by "about" or "approximately" the indicated value, and take into account experimental error and variations that would be expected by a person having ordinary skill in the art.

UVA-irradiation was found to generate cyclobutane dimers at TT and to a lower extent at TC sites as a likely result of energy transfer mechanism involving still unknown photoexcited chromophore(s). Oxidative damage to DNA is also induced although less efficiently by UVA-mediated photosensitization processes than UVB. UVA mostly involves singlet oxygen species together with a smaller contribution of hydroxyl radical-mediated reactions through initially generated superoxide radicals.

A radical chain reaction inhibitor is commonly regarded as an antioxidant. The human skin deploys a rich complement of antioxidant mechanisms against various forms of oxidative stress. These biological antioxidant mechanisms can be broken down by enzymatic and non-enzymatic. Enzymatic mechanisms include, but are not limited to, superoxide dismutase, catalase and gluthione peroxidase. Non-enzymatic mechanisms include, but are not limited to, antioxidant enzyme cofactors (Se, coenzyme Q10), oxidative enzyme inhibitor (aspirin ibuprofen), transmission metal chelators (EDTA) and radical scavengers (such as Vitamin C and E).

Reactive oxygen species (ROS) are responsible for oxidative stress. It has been discovered that there are six major reactive oxygen species causing oxidative damage in the human body. These species are superoxide anion ($O_2.$), hydrogen peroxide ($H_2O_2.$), peroxyl radicals (ROO.), hydroxyl radical (HO.), singlet oxygen ($^1O_2.$), and peroxynitrate (ONOO.). To counteract the assault of these ROS, living cells have a biological defense system composed of enzymatic antioxidants that convert ROS/RNS to harmless species. For example super oxide ion $(O_2.)^-$ is converted to oxygen by catalase. In contrast, no enzymatic action is known to scavenge ROO., HO., $^1O_2.$, and ONOO.. Therefore, the burden of defense relies on a variety of nonenzymatic antioxidants, such as vitamins C and E and many chemicals, which have the property of scavenging oxidants and free radicals. To comprehensively evaluate the oxidant-scavenging capacity of a sample, assays have to be designed to include these ROS. However, the majority of assays are designed to measure a sample's capacity to react with one oxidant (either organic radical or redox active compounds). The peroxyl radical has been the most frequently used ROS in the assays because it is a key radical in auto-oxidation and it can be easily generated.

A multitude of in vitro antioxidant capacity assays have been developed. The application of these in vitro assays in clinical research are limited due to the following: from being based on chemical reactions in vitro, though similarly to biological systems that can only be implied by the reaction mechanism involved, through the pH of the media, and through the standard redox potentials that are similar to those involved in cellular reactions. Non-limiting exemplary in vitro antioxidant capacity assays include the ORAC (oxygen radical absorbance capacity), the TRAP (total radical trapping antioxidant parameter), the Crocin bleaching assay, the IOU (inhibited oxygen uptake), the inhibition of linoleic acid oxidation, the inhibition of LDL oxidation, the TEAC (Trolox equivalent antioxidant capacity), the FRAP (ferric ion reducing antioxidant capacity), the DPPH (diphenyl-1-picrylhydrazyl), the copper (II) reduction capacity, the total phenols assay by Folin-Ciocalteu reagent, the TOSC (total oxidant scavenging capacity), chemiluminescence, electrochemiluminescence, and the inhibition of Briggs-Rauscher oscillation method (BROM).

It is problematic to apply antioxidant capacity assays to an inhomogeneous biological substrate like the human skin. The epidermis contains no blood cells and only the cells in the deeper layer receive blood by diffusion from blood capillaries that extend to the upper layers of the dermis. Also the concentration gradient of water content varies from very low water content in the stratum corneum to higher water content in the basal layer of the epidermis. The oversimplified division of antioxidants in water soluble or lipid soluble is not really useful of their specific roles in the chemical kinetics of skin cellular damage. The basic kinetic models of inhibited auto-oxidation depend on the chemical reactions involved. Some compounds contribute to the antioxidant defense by scavenging the free radicals while others by their ability to chemically reduce the oxidants present.

The mechanism of reactions for antioxidant capacity are divided in two types of kinetics, hydrogen atom transfer (HAT) and electron transfer (ET). The majority of HAT-based assays apply a competitive reaction scheme, in which antioxidant and substrate compete for thermally generated peroxyl radicals. In contrast, ET-based assays measure the capacity of an antioxidant in the reduction of an oxidant, when reduced. The degree of antioxidant capacity is correlated with the sample's antioxidant concentrations. ET-based assays include, but are not limited to, the Trolox equivalence antioxidant capacity, the ferric ion reducing antioxidant power (FRAP), and the Briggs-Rauscher Oscillation Reaction Method (BROM).

The Applicant has discovered the unexpected benefits of using an ET-based in-vitro antioxidant assay in predicting the performance of antioxidants in protecting the outer layers of human skin from the harmful effects of UV radiation. The BROM (Briggs-Rauscher) oscillations are potentiometrically followed by using a bright platinum electrode coupled with a suitable reference electrode. The main intermediates for which concentrations oscillate in the BR reaction are iodine; iodine ion; oxyiodine species HOI, HOIO, and $IO_2$; and the hydroperoxyl radical HOO.. In the onset of oscillations have been previously recognized in the chemical literature. The assay method based on the inhibitory effects of antioxidants on the oscillations of hydrogen peroxide induced free radicals has been discovered by the Applicant to be predictive of which antioxidants may be more effective protecting the shallow layers of the skin (epidermal layer) with low water content against the harmful effects of UV radiation. The BROM has been discovered by the Applicant to provide closer kinetic requirements to those present in different layers of the skin. The BROM method is relatively new in the determination of antioxidant capacity of many chemical compounds. The somewhat apparently low values for "well known" antioxidants like Vitamin E (0 oscillations sec/ug) and vitamin C (0.00105 sec/ug) can be easily explained by the reaction conditions, and how the kinetic transfer associated with the method works.

The BROM method is used for the selection of preferred antioxidants to be used in the upper layers of the skin with low water content. The BROM electron transfer method takes place at a redox of 500 mV in acid conditions and antioxidant capacity can be determined in solvents with little water content. The BROM method detects the electron transfer current present where antioxidants and hydrogen peroxide are allowed to react and has been discovered to be predictive of the electrophilic nature of antioxidants that act as electron or photon traps in the upper layers of the skin.

Table 2 below gives the BROM values for common antioxidants present in body fluids and tissues.

TABLE 2

| Antioxidant metabolite | Solubility | Concentration in human serum (μM) | Concentration in liver tissue (μmol/kg) | BROM [s/μg] |
|---|---|---|---|---|
| Ascorbic acid (vitamin C) | Water | 50-60 | 260 (human) | 0.00105 |
| Glutathione | Water | 4 | 6,400 (human)[1] | 0.000991 |
| Uric acid | Water | 200-400 | 1,600 (human) | 9.14 |
| Carotenes | Lipid | β-carotene: 0.5-1 retinol (vitamin A): 1-3 | 5 (human, total carotenoids) | 0 (Tretinoin) |
| α-Tocopherol (vitamin E) | Lipid | 10-40 | 50 (human) | 0 |
| Ubiquinol (coenzyme Q10) | Lipid | 5 | 200 (human) | 0 |

In Table 3 below, the BROM antioxidant capacity for some of the antioxidant metabolites listed in Table 2 and some other additional antioxidant compounds are listed from lowest to highest values.

TABLE 3

Table 3 - Antioxidants by BROM strength

BROM by Strength

| | Sample Size [μg] | Solvent | Result [s/μg] |
|---|---|---|---|
| Allantoin | 7700 | Water | 0 |
| D-Glucose | 700000 | Water | 0 |
| Oxybenzone | 7500 | Ethanol | 0 |
| Solastay S1 | 1600 | Ethanol | 0 |
| Tretinoin | 1700 | Ethanol | 0 |
| Vitamin E Acetate | 33000 | Ethanol | 0 |
| Ascorbyl Glucoside | ≈1300 | Water | No clear result |
| Triethanolamine Salicylate | 2500 | Water | No clear result |
| Glutathione | 12000-15000 | Water | 0.000991 |
| Ascorbic Acid | 10000-100000 | Water | 0.00105 |
| Trolox | 1000-6000 | Ethanol | 0.021 |
| Tert-Butylhydroquinone | 1200-1900 | Ethanol | 0.13 |
| Grapefruit Peel | 300-1300 | 50% Ethanol | 0.38 |
| Hydroquinone | 40582 | 50% Ethanol | 1.1 |
| Hydroquinone | 40582 | Water | 1.31 |
| Hesperidin | 40735 | Water | 5.38 |
| Polyphenols | 40672 | Water | 6.52 |
| Atorvastatin (Lipitor) | 22-32 | Ethanol | 8.41 |
| Uric Acid | 130-180 | Water | 9.14 |
| Resveratrol | 40609 | Ethanol | 18.34 |
| BHT | 40639 | Ethanol | 29.4 |
| Resorcinol | 40742 | Water | 30.39 |
| BHT | 40645 | 50% Ethanol | 34.53 |
| β Arbutin | 40739 | Water | 40.53 |
| Arbutin Racemic mixture | 40711 | 50% Ethanol | 47 |
| Arbutin Racemic mixture | 40678 | Water | 49.4 |

The results indicate that arbutin, butylatedhydroxytoluene (BHT), resorcinol, resveratrol, atorvastatin, uric acid, polyphenols, and hesperidin all have BROM values greater than 5 s/μg. The results of Table 3 are unexpected in that well known antioxidants like vitamin C (ascorbic acid), Trolox (vitamin E derivative) and vitamin E acetate do not show measurable electron scavenging capacity. The results also indicate that only those antioxidants with electrophilic groups will be effective in the upper layers of the skin where the photon induced damage occurs in low water content media and no reducing conductivity occurs. Therefore, it has been discovered that preferred antioxidants to act as free radical scavengers are molecules with highly electrophilic functional groups. The highest BROM values were obtained for certain substituted phenolic or polyphenolic compounds with aromatic rings that could easily react with unpaired electrons. Based on BROM values listed above, it is predicted that the selected agents for better protection against phototoxic free radical molecules should be the substituted phenolics, such as arbutin and butylatedhydroxytoluene (BHT). However, antioxidants with BROM capacities greater than 5 sec/ug will have similar effects when added in sufficient concentrations to provide the concentration threshold of antioxidants needed.

The Applicant has also discovered that various combinations of antioxidants are effective for use in sun screens, lip balms and other topically applied skin care products for protecting the skin from UV radiation. These antioxidant combinations include an effective amount of two, or three, or four or more individual antioxidants, wherein an effective amount is defined as a concentration of antioxidants in the skin care product that results in a measured BROM value of the antioxidant mixture that is greater than the sum of the BROM values of the individual antioxidants in the mixture at the same concentration. When the antioxidant mixture in the product includes two antioxidants, the relative ratio of the two may be from 1:4 to 4:1, or 1:3 to 3:1, or 1:2 to 2:1, or 1:2 to 1:1, or 1:1. When the antioxidant mixture in the product includes three antioxidants, the relative ratio of the three may be from 1:1:4 to 4:1:1, or 1:1:3 to 3:1:1, or 1:1:2, to 2:1:1, or 2:1:1 to 2:1:4, or 1:1:1 to 2:1:2. The following antioxidant mixtures including two antioxidants have been found to yield a synergistic impact on the measured BROM values, that is, the measured BROM value of the antioxidant mixture in the product is greater than the sum of the BROM values of the individual antioxidants in the mixture at the same concentration: arbutin/BHT, atorvastatin/BHT, arbutin/hydroquinone, hydroquinone/BHT, atorvastatin/uric acid, arbutin/resveratrol, BHT/resveratrol, and atorvastatin/hydroquinone. These antioxidant mixtures, which include two antioxidants, may also optionally include a third antioxidant (which is different from the first two) at an effective amount to further reduce the measured BROM value of the mixture relative to the sum of the BROM values of the individual antioxidants in the mixture at the same concentration, wherein the third antioxidant is chosen from atorvastatin, BHT, hydroquinone, resveratrol, arbutin, uric acid and combinations thereof.

The following antioxidant mixtures including three antioxidants have been found to yield a synergistic impact on the measured BROM values, that is, the measured BROM value of the antioxidant mixture in the product is greater than the sum of the BROM values of the individual antioxidants in the mixture at the same concentration: uric acid/atorvastatin/BHT, arbutin/hydroquinone/BHT, and arbutin/BHT/resveratrol. These antioxidant mixtures, which include three antioxidants, may also optionally include a fourth antioxidant (which is different from the first three) at an effective amount to further reduce the measured BROM value of the mixture relative to the sum of the BROM values of the individual antioxidants in the mixture at the same concentration, wherein the fourth antioxidant is chosen from atorvastatin, BHT, hydroquinone, resveratrol, arbutin, uric acid and combinations thereof.

Each of these two and three component mixtures of antioxidants identified by the Applicant may also yield a measured BROM value of the skin type product is greater than or equal to 0.2 sec/μg, or 0.25 sec/μg, or 0.30 sec/μg, or 0.35 sec/μg, or 0.40 sec/μg, or 0.45 sec/μg, or 0.50 sec/μg, or 0.55 sec/μg, or 0.60 sec/μg, or 0.65 sec/μg, or 0.70 sec/μg, or 0.75 sec/μg, there is sufficient protection from the harmful effects of UV radiation on the outer layers of the skin. Each of these two and three component mixtures of antioxidants identified by the Applicant may also yield a phototoxic potential as measured by the 3T3 Neutral Red Phototoxicity Test that is at least 5% lower, or 10% lower, or 15% lower, or 20% lower, or 25% lower, or 30% lower, or 35% lower, or 40% lower, or 45% lower, or 50% lower relative to the control solution (non phototoxic and no antioxidants) at a solution concentration range of from 0.0001-0.002%. Alternatively, the concentration of the inventive antioxidant mixtures in the finished skin type product may range from 0.0002 to 0.0018%, or 0.0004 to 0.0016%, or 0.0006 to 0.0014%, or 0.0008 to 0.0012%, or 0.0009 to 0.0011%.

The inventive antioxidants mixtures described above may be utilized in a host of topically applied skin care products requiring UV protective capacity. Non-limiting exemplary skin care products include sunscreens, lip sticks, lip balms, skin whiteners, cosmetic products, pharmaceutical products and dermatological products.

The following are examples of the present disclosure and are not to be construed as limiting.

EXAMPLES

BROM Measurements

In Table 4 below, the BROM values of different combinations of antioxidant compounds have been measured to determine antioxidant capacity.

TABLE 4

BROM by Strenght

| Ingredient | Ratio | Sample Size [μg] | Solvent | Result [s/μg] | Theoretical Result [s/μg] | (R/TR − 1) * 100 [%] |
|---|---|---|---|---|---|---|
| Hydroquinone | 11 | 41-192 | Water | 0.55 | 0.46 | 18.65 |
| Glucose | 18 | | | | | |
| BHT | 1 | 32-69 | 50% Ethanol | 1.6 | 1.59 | 0.57 |
| Hydroquinone | 80 | | | | | |
| Ascorbic Acid | 1 | | 50% Ethanol | 1.96 | 2.8 | −29.87 |
| Atorvastatin | 1 | 100-140 | | | | |
| Vit E Acetate | 1 | | | | | |
| BHT | 1 | 16-54 | 50% Ethanol | 2.2 | 1.96 | 12.33 |
| Hydroquinone | 40 | | | | | |
| Atorvastatin | 1 | | 50% Ethanol | 2.76 | 4.12 | −32.91 |
| Vit E Acetate | 1 | 78-127 | Ethanol | | | |
| Ascorbic Acid | 1 | 50-78 | 50% Ethanol | 3.31 | 4.24 | −21.97 |
| Atorvastatin | 1 | | | | | |
| BHT | 1 | 40678 | 50% Ethanol | 8.04 | 7.36 | 9.19 |
| Hydroquinone | 4 | | | | | |
| Atorvastatin | 1 | 31-55 | 50% Ethanol | 13 | 8.89 | 46.2 |
| Uric Acid | 2 | | | | | |
| Atorvastatin | 2 | 29-40 | 50% Ethanol | 14.29 | 8.64 | 65.39 |
| Uric Acid | 1 | | | | | |
| Arbutin | 1 | 18598 | Water | 15.37 | 10.1 | 52.15 |
| Hydroquinone | 4 | | | | | |
| Ascorbic Acid | 1 | 35-55 | 50% Ethanol | 18.86 | 18.1 | 4.4 |
| Atorvastatin | 1 | | | | | |
| BHT | 2 | | | | | |
| Atorvastatin | 1 | 24-37 | 50% Ethanol | 19.19 | 8.79 | 118.41 |
| Uric Acid | 1 | | | | | |
| BHT | 1 | 40783 | Water | 19.61 | 23.05 | −14.92 |
| Resveratrol | 2 | | | | | |
| Arbutin | 2 | | 50% Ethanol | 22.58 | 18.26 | 23.64 |
| BHT | 1 | 16-38 | | | | |
| Hydroquinone | 4 | | | | | |
| Atorvastatin | 1 | 40-63 | 50% Ethanol | 26.56 | 20.21 | 31.38 |
| BHT | 1 | | | | | |
| Atorvastatin | 1 | 40-67 | 50% Ethanol | 28.37 | 24.12 | 17.61 |
| BHT | 2 | | | | | |
| Arbutin | 2 | | 50% Ethanol | 32.77 | 32.84 | −0.2 |
| Atorvastatin | 1 | 40771 | Ethanol | | | |
| BHT | 1 | | | | | |
| Arbutin | 1 | 13-14 | 50% Ethanol | 33.41 | 36.42 | −8.28 |
| BHT | 2 | | | | | |
| Arbutin | 1 | 40648 | Water | 35 | 31.26 | 11.95 |
| Resveratrol | 1 | | | | | |
| Arbutin | 1 | 40680 | 50% Ethanol | 35.23 | 38.82 | −9.27 |
| BHT | 1 | | | | | |
| Arbutin | 2 | | 50% Ethanol | 36.5 | 30.94 | 17.98 |
| BHT | 1 | 40716 | Ethanol | | | |
| Hydroquinone | 1 | | | | | |
| Arbutin | 2 | 40711 | 50% Ethanol | 41.19 | 41.13 | 0.14 |
| BHT | 1 | | | | | |
| Arbutin | 2 | 40780 | Water | 44.85 | 31.65 | 41.69 |
| BHT | 1 | | | | | |
| Resveratrol | 2 | | | | | |
| Arbutin | 4 | 40708 | 50% Ethanol | 45.4 | 42.9 | 5.82 |
| BHT | 1 | | | | | |

The results in Table 4 indicate that in some instances a synergistic increase of antioxidant capacity occurs by combining two or more antioxidants. This is indicated by an actual result over a theoretical result ((R/TR−1)*100) that is positive and greater than 1. The largest synergistic increases are observed for different ratios of arbutin and hydroquinone, atorvastatin and uric acid, arbutin and BHT and atorvastatin with BHT.

In Table 5 below, the BROM values for different combinations of arbutin and hydroquinone were measured. The ratio of arbutin to hydroquinone ranged from 4:1 to 1:4.

Throughout the range of ratios, the BROM values of the combinations of arbutin and hydroquinone yield a reducing capacity that is significantly improved relative to the BROM values of the individual antioxidant ingredients. Hence, the combination of arbutin and hydroquinone results in a synergistic improvement in BROM values over the range of ratios of arbutin to hydroquinone ranging from 4:1 to 1:4. Arbutin and hydroquinone are substituted phenolics, which are used as skin whitening agents. The combinations of substituted phenolics with synergistic BROM values indicate their potential effectiveness as skin whitening combinations in cosmetic and pharmaceutical products.

TABLE 5

BROM

| Ingredient | Ratio | Sample Size [µg] | Solvent | Result [s/µg] | Theoretical Result [s/µg] | (R/TR − 1) * 100 [%] |
|---|---|---|---|---|---|---|
| Arbutin | 4 | 40766 | Water | 44.72 | 36.76 | 21.64 |
| Hydroquinone | 1 | | | | | |
| Arbutin | 2 | 40828 | Water | 33.13 | 30.73 | 7.79 |
| Hydroquinone | 1 | | | | | |
| Arbutin | 1 | 25-37 | Water | 25.28 | 15.89 | 59.08 |
| Hydroquinone | 2 | | | | | |
| Arbutin | 1 | 18598 | Water | 15.37 | 10.1 | 52.15 |
| Hydroquinone | 4 | | | | | |

Therefore any synergism present when using a combination of the two best known skin lightening agents i.e. arbutin and hydroquinone (HQ) may allow one the ability to formulate a skin lightening product with maximum efficacy and minimum toxicity. HQ reduces all three components of melanin production, that is, tyrosinase, melanin, and melanocytes. Hydroquinone is toxic to melanocytes. Arbutin inhibits tyrosinase; reduces melanin and is not toxic to melanocytes. Therefore, the synergism between arbutin and hydroquinone will allow their use as more effective skin lightening agents with lower toxicity.

Another unexpected finding is the increased antioxidant capacity of a blend of two parts Arbutin by weight with one part of BHT and two parts of resveratrol. This blend shows an increase of approximately 40% more than the contribution of the individual antioxidants. To test the hypothesis that Arbutin, BHT and resveratrol will be beneficial in protecting the free radical damaging effects of UV radiation the three antioxidants were prepared in a carrier of mixture of polysorbate 20, propylene glycol and ethanol. A control solution did not have an antioxidant (control). The free radical scavengers tested were arbutin/BHT (Sample 1 or S1), resveratrol (Sample 2 or S2), and resveratrol plus arbutin and BHT (Sample 3 or S3). The control and the S1, S2 and S3 solution were then exposed to the 3T3 Neutral Red Phototoxic Test described below and the BROM values were measured for each. The BROM test results are included in Table 6 below. The results show that each of S1, and S3 have high BROM values, while S2 only has approximately $\frac{1}{10}^{th}$ the BROM values of the other two. S1 and S3 with the higher BROM value are effective in protecting murine fibroblast cells tested against the harmful effects of the high intensity simulated sunlight source, while S2 is phototoxic to the cells.

Toxicological Testing:

In addition to BROM values, cytotoxicity and phototoxicity measurements were made on the control, S1, S2 and S3 solutions. The 3T3 Neutral Red Phototoxicity Test (3T3 NRU PT) was used to assess toxicological performance. It is a relatively new assay that was adopted by regulatory agencies such as OECD and FDA as an accepted method for the assessment of phototoxic potential of test substances. It is an in-vitro toxicological assessment test used to determine cytotoxic and photo(cyto)toxicity effect of a test article to murine fibroblasts in the presence or absence of UVA light (99% UVA/1% UVB). The 3T3 Neutral Red Uptake Phototoxicity Assay (3T3 NRU PT) can be utilized to identify the phototoxic effect of a test substance induced by the combination of test substance and light and is based on the comparison of the cytotoxic effect of a test substance when tested after the exposure and in the absence of exposure to a non-cytotoxic dose of UVA/vis light. Cytotoxicity is expressed as a concentration dependent reduction of the uptake of the vital dye—Neutral Red. Substances that are phototoxic in-vivo after systemic application and distribution to the skin, as well as compounds that could act as phototoxicants after topical application to the skin can be identified by the test. The reliability and relevance of the 3T3 NRU PT have been evaluated and has been shown to be predictive when compared with acute phototoxicity effects in vivo in animals and humans.

Figure 2:
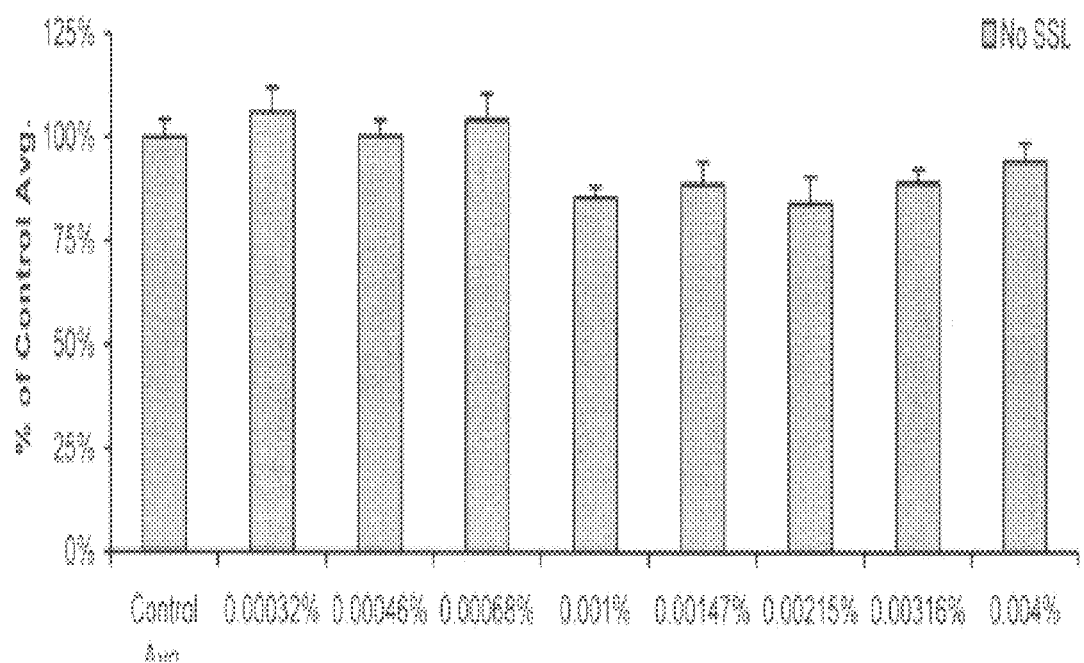
FIG. 2 is a bar graph of % cytotoxicity relative to a control of Sample 1 (JR-42-24C) as a function of concentration of JR-42-24C in the solution.
Figure 3:
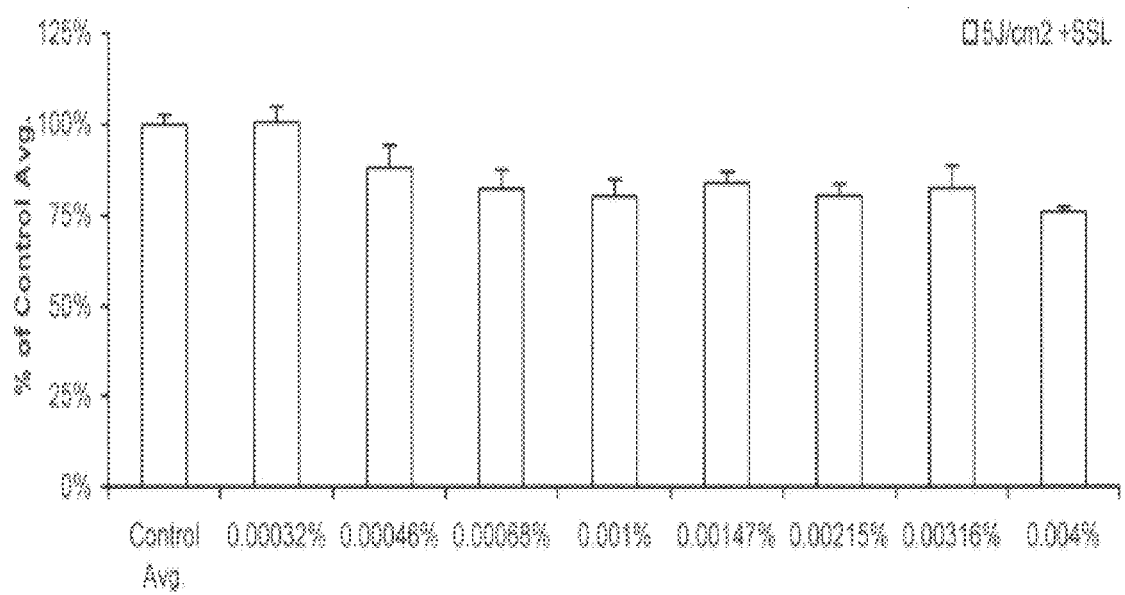
FIG. 3 is a bar graph of % photocytotoxicity relative to a control of Sample 1 (JR-42-24C) as a function of concentration of JR-42-24C in the solution.
Figure 4:
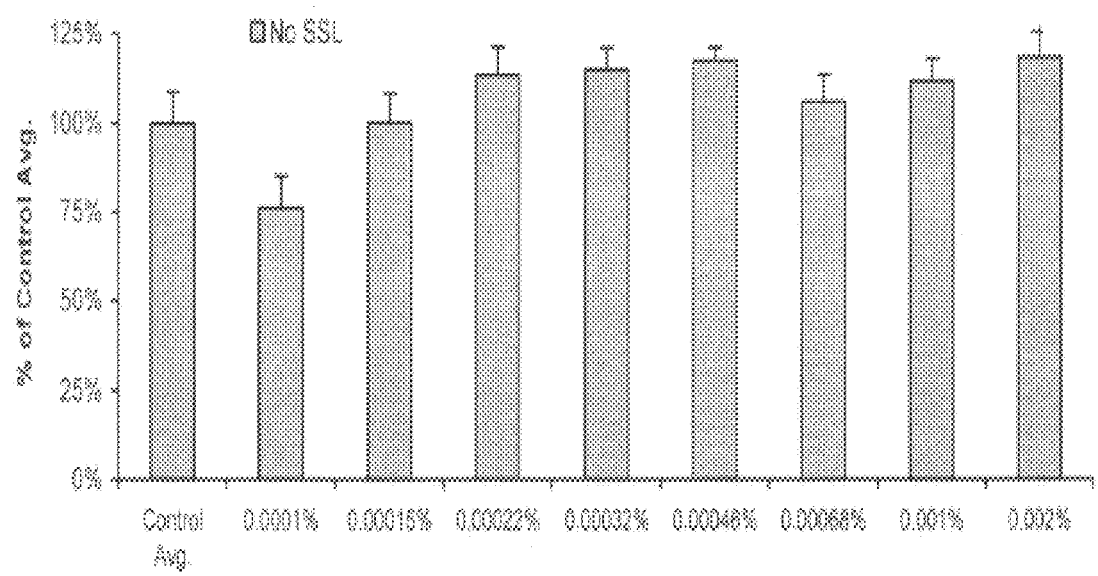
FIG. 4 is a bar graph of % cytotoxicity relative to a control of Sample 2 (JR-42-26A) as a function of concentration of JR-42-26A in the solution.
Figure 5:
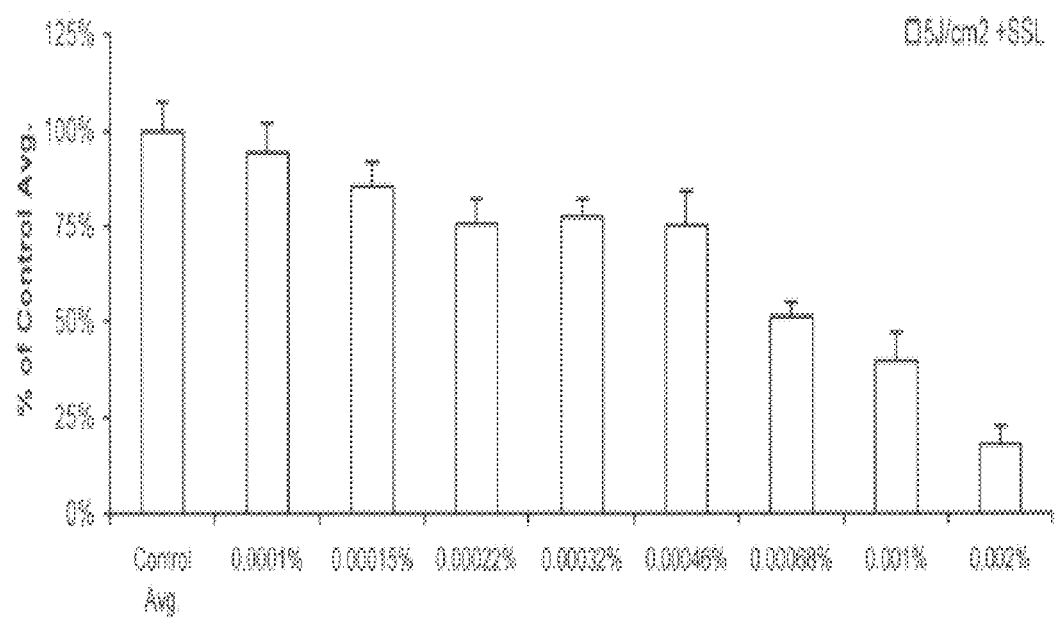
FIG. 5 is a bar graph of % photocytotoxicity relative to a control of Sample 2 (JR-42-26A) as a function of concentration of JR-42-26A in the solution.
Figure 6:
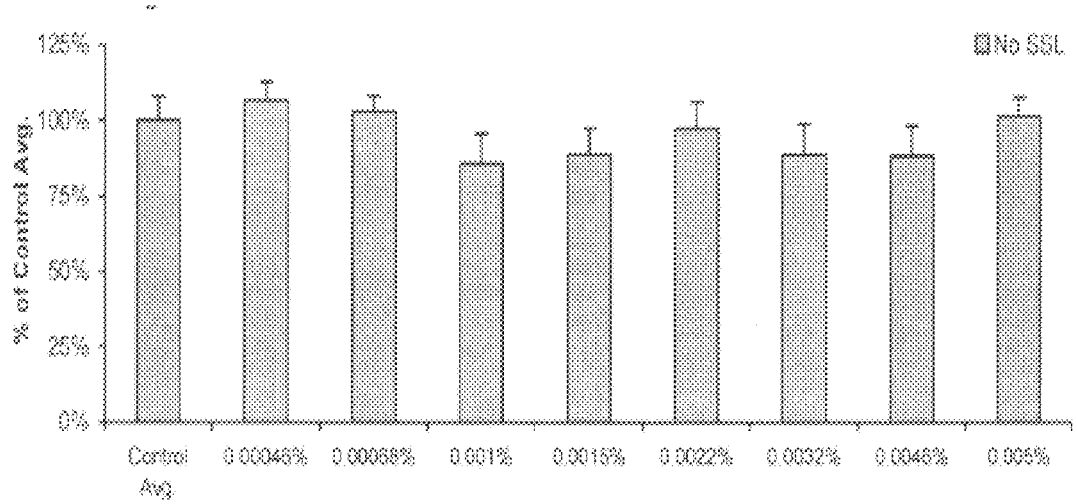
FIG. 6 is a bar graph of % cytotoxicity relative to a control of Sample 3 (JR-42-26C) as a function of concentration of JR-42-26C in the solution.
Figure 7:
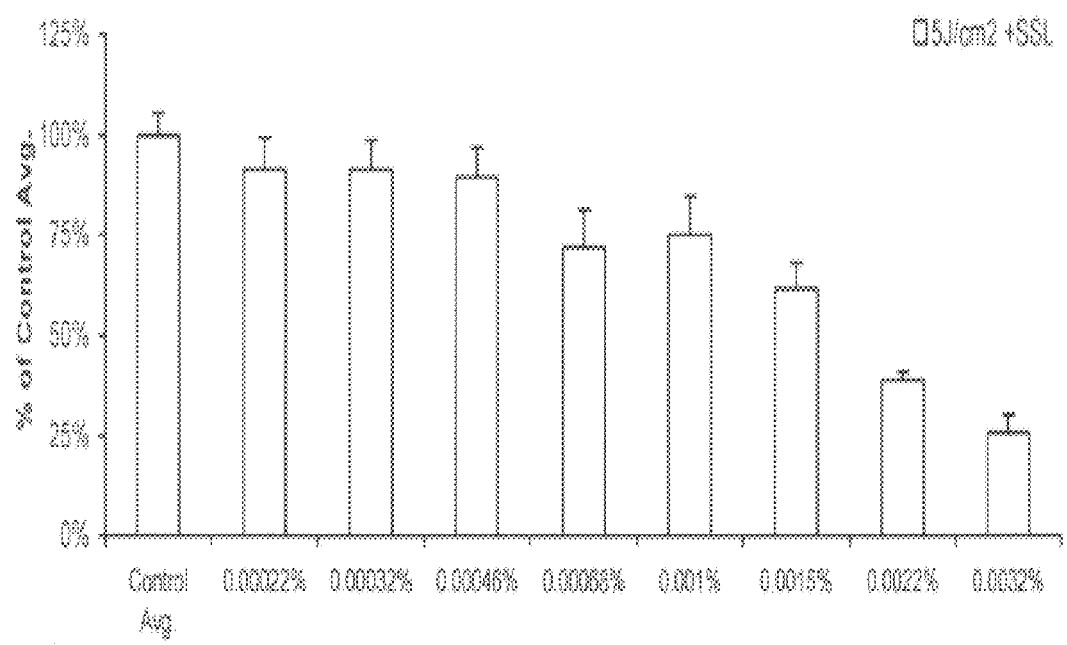
FIG. 7 is a bar graph of % photocytotoxicity relative to a control of Sample 3 (JR-42-26C) as a function of concentration of JR-42-26C in the solution.

To test the hypothesis that arbutin and BHT (both substituted phenolics) will either individually or in combinations be beneficial in protecting the free radical damaging effects of UV radiation, different solutions were prepared for testing as indicated in Table 8 below. The different solutions included a control (carrier with not antioxidants) as well as test solutions including the carrier with antioxidants for free radical scavenging (S1:Control+arbutin/BHT, S2:Control+Resveratrol, and S3:Control+Resveratrol plus arbutin and BHT). The four solutions were exposed to the BROM, and 3T3 Neutral Red Phototoxic Test and the results are indicated in Table 6 below with regard to BROM values and FIGS. 2-7 with regard to cytotoxicity and photocytotoxicity results for Samples S1, S2 and S3. The x-axis for each of the bar graphs are in units of concentration of the free radical scavenging antioxidants in the solution. The results depicted FIGS. 2-7 indicate that certain antioxidant combinations in a carrier solution decrease the phototoxic potential as measured by cytotoxicity and phototoxicity via the 3T3 Neutral Red Phototoxicity Test by at least 5%, or 10%, or 15%, or 20%, or 25%, or 30%, or 35%, or 40%, or 45%, or 50% relative to the control solution (non phototoxic and no antioxidants) at a solution concentration range of from 0.0001-0.002%. The carrier solution for the antioxidant formulation may be a pharmaceutical, cosmetic or dermatological carrier for pharmaceutical, cosmetic or dermatological products.

TABLE 6

| | Sample | | | |
|---|---|---|---|---|
| | Control | S1 | S2 | S3 |
| Designation | JR-42-24A | JR-42-24C | JR-42-26A | JR-42-26C |
| Arbutin | | 0.2 | | 0.2 |
| BHT | | 0.1 | | 0.1 |
| Resveratrol | | | 0.2 | 0.2 |
| Polysorbate 20 | 0.5 | 0.5 | 0.5 | 0.5 |

TABLE 6-continued

| | Sample | | | |
|---|---|---|---|---|
| | Control | S1 | S2 | S3 |
| Polypropylene Glycol | 0.3 | 0.1 | 0.3 | |
| Ethanol | 99.2 | 70.1 | 99 | 99 |
| Water | | 29 | | |
| Total | 100 | 100 | 100 | 100 |
| BROM [s/ug] (of solution) | 0 | 0.166 | 0.022 | 0.222 |

For both the range finding screen and the definitive test, Balb/c 3T3 cells were seeded in the central 60 wells of duplicate 96-well microplates per test article and maintained in culture for 24 hours. The well 96-well plates were then preincubated with eight different concentrations of each test article for one hour. After preincubation, one plate was irradiated with a dose of 5 J/cm**2. Solar Simulated Light (SSL, containing wavelengths in the UVA and visible regions with >99% of UVB blocked out), while the duplicate plate was kept in the dark (no SSL). After UV irradiation, the treatment medium was replaced with culture medium and after 24 hours, cell viability was determined by neutral red uptake for 3 hours.

Test articles JR-42-24C sample 1, JR-42-26A sample 2, and JR-42-26C were phototested. Test articles JR-42-24C Sample 1, JR-42-26A Sample 2, and JR-42-26C Sample 3, provided by the Sponsor, were tested in a 3T3 Neutral Red Uptake Phototoxicity Test using the Sponsor-provided vehicle JR-42-24A. Range finding screens were performed to determine the acceptable concentrations for the definitive test. Microsoft Excel® was used to calculate the $EC_{50}$ values and Photo-irritant Factor (PIF) for the test articles and the Chloropromazine (CPZ) positive control in both the screen and the definitive test. Results of the definitive tests are shown in Table 7 below:

TABLE 7

| Test Article | Concentration Range Tested | $EC_{50}$ No SSL | $EC_{50}$ + SSL | PIF |
|---|---|---|---|---|
| JR-42-24C Sample 1 | 0.00032-0.004% | >0.004% | >0.004% | None |
| JR-42-26A Sample 2 | 0.0001-0.002% | >0.002% | 0.00071% | >2.8 |
| JR-42-26C Sample 3 | No SSL: 0.00046-0.005% + SSL: 0.00022-0.0032% | ND | ND | ND |
| CPZ Positive Control | No SSL: 6.81-100 µg/ml + SSL: 0.22-3.16 µg/ml | | | |
| | dose date Mar. 10, 2011 | 19.592 µg/ml | 0.394 µg/ml | 49.67 |
| | dose date Mar. 15, 2011 | 24.605 µg/ml | 0.725 µg/ml | 34.19 |
| | dose date Mar. 22, 2011 | 26.457 µg/ml | 0.682 µg/ml | 38.80 |

From Table 7, it can be seen that the test article JR-42-24C Sample 1 is considered not to have phototoxic potential in the 3T3 Neutral Red Uptake Phototoxicity Test. The range of antioxidants tested in sample 1 would have been 300× more diluted than the concentration range tested (0.0003-0.0040). Test article JR-42-26A Sample 2 with 0.2% resveratrol is considered to have probable phototoxic potential in the concentration range tested (0.0001-0.002%) in the 3T3Neutral Red Uptake Phototoxicity Test. Test article sample 3, JR-42-26C has 0.2% resveratrol to which 0.1% BHT and 0.2% arbutin were added. Test article JR-42-26C Sample 3 was initially phototoxic in the 3T3Neutral Red Uptake Phototoxicity Test, but PIF values declined over time to non-phototoxic levels. The results indicated that although some phototoxicity is present the concentration range tested, but increased 4 times more than the samples without arbutin and BHT (sample 2). The conclusion obtained is the expected effect of adding the arbutin and BHT to the somewhat phototoxic resveratrol. In addition, the phototoxic protection suggested by the combination of arbutin and BHT indicates that even when exposed to the minimal erythemal dose (MED) of more than 250 times, the mili-molar presence of the free radical scavengers is sufficient to protect fibroblast cells exposed 250 times the MED from phototoxic products resulting from the degradation of chromophores as shown in the 3T3 Neutral Red Phototoxic Test. As shown in Table 7, even though a phototoxic material is present, the phototoxicity of the test sample is decreased by a factor of 4.

Empirically it was determined that by the addition of 0.2% Arbutin and 0.1% BHT to Sample 2, which then became Sample 3, the BROM value was increased from 0.02 sec/µg (Sample 2) to 0.2 sec/µg (Sample 3). This 10 fold increase in BROM value proved to be effective in providing phototoxicity protection to the fibroblast cells using the 3T3 Test. The non-phototoxic results were also obtained for Sample 1 with a BROM value of 0.166 sec/µg.

As an empirical guideline, in order to determine an effective protection factor for a finished product (FP), the Applicant has derived the following relationship:

BROM FP≥0.2 sec/µg % antioxidant needed for sunprotection=antioxidant combination or individual BROM value÷100

The Applicant has discovered that when the BROM value of the finished product is greater than or equal to 0.15 sec/µg, or 0.2 sec/µg, or 0.25 sec/µg, or 0.30 sec/µg, or 0.35 sec/µg, or 0.40 sec/µg, or 0.45 sec/µg, or 0.50 sec/µg, or 0.55 sec/µg, or 0.60 sec/µg, or 0.65 sec/µg, or 0.70 sec/µg, or 0.75 sec/µg, there is sufficient protection from the harmful effects of UV radiation on the outer layers of the skin.

For example, with an antioxidant combination of Arbutin at 0.2 wt. % and BHT at 0.1 wt. %, the Arbutin BROM value of 50 sec/µg×0.2% (multiply by 0.002)=BROM of 0.1 and the .BHT BROM value of 30 sec/µg×0.1% (multiply by 0.001)=BROM value 0.03. The antioxidant combination yields a calculated BROM value of approximately 0.13 (=0.1+0.03). Sample 1 has an actual BROM value of 0.166 sec/µg and therefore there is a slight synergistic increase when Arbutin and BHT are combined. The above relationship is an empirical guideline and one should measure the actual BROM value for the finished product and also conduct photocytotoxicity and cytotoxicity testing as necessary.

In Table 8 below are BROM values for commercial products without the addition of arbutin and BHT.

TABLE 8

Product BROM by Strength

| | Sample Size [μg] | Solvent | Result [s/μg] |
|---|---|---|---|
| Covergirl Nature Luxe 270 Gloss Balm SPF15 | 5700 | Ethanol | 0 |
| CVS Sport Sunscreen SPF 15 | 71000 | Ethanol | 0 |
| CVS Sport Sunscreen SPF 30 | 15000 | 50% Ethanol | 0 |
| CVS Sport Sunscreen SPF 50 | 64000 | Ethanol | 0 |
| CVS Ultra Dry Sheer Lotion Sunscreen SPF 30 | 25000 | 50% Ethanol | 0 |
| Neutrogena Age Shield Face Sunblock SPF 55 | 18000 | 50% Ethanol | 0 |
| Neutrogena Moisture Shine Lip Soother Cooling Hydragel SPF20 | 18000 | Ethanol | 0 |
| Neutrogena Ultra Sheer Dry-Touch Sunblock SPF30 | 24000 | 50% Ethanol | 0 |
| Rimmel Moisture Renew 740 Auburn Breeze SPF18 | 16000 | Ethanol | 0 |
| Rimmel Moisture Renew Cream Lipgloss SPF15 | 23000 | Ethanol | 0 |
| Australian Gold | 19000-31000 | 50% Ethanol | 0.003 |
| Clinique Dark Spot Corrector | 430-1000 | 50% Ethanol | 0.067 |

The results in Table 8 indicate that the BROM values for commercial products are very low and therefore would be predicted to offer minimal protection to the outer layers of the skin to the harmful effects of UV radiation.

In Table 9 below are BROM values for commercial products with the addition of Arbutin and optionally BHT.

TABLE 9

BROM Alphabetical 1 of 1

| | Antioxidant Added | | Sample | | Result | Theoretical BROM | (BROM/TBROM − 1) * 100 [%] | Date |
|---|---|---|---|---|---|---|---|---|
| | Name | Amount [%] | Size [μg] | Solvent | [s/μg] | [s/μg] | | |
| Australian Gold | Arbutin BHT | 0.5 0.25 | 700-2000 | 50% Ethanol | 0.390 | 0.311 | 25.4 | Mar. 25, 2011 |
| Clinique Dark Spot Corrector | Arbutin | 1 | 150-1500 | 50% Ethanol | 0.760 | 0.528 | 61.0 | Dec. 2, 2010 |
| CVS Sport Sunscreen SPF 15 | Arbutin BHT | 0.5 0.25 | 1400-1900 | 50% Ethanol | 0.33 | 0.308 | 8.4 | May 2, 2011 |
| CVS Sport Sunscreen SPF 30 | Arbutin BHT | 0.5 0.25 | 1700-2000 | 50% Ethanol | 0.29 | 0.308 | −4.5 | May 2, 2011 |
| CVS Sport Sunscreen SPF 50 | Arbutin BHT | 0.5 0.25 | 1600-2000 | 50% Ethanol | 0.28 | 0.308 | −8.9 | May 4, 2011 |

The results in Table 9 indicate that the Australian Gold, Clinique dark spot corrector and CVS sport sunscreen SPF 15 all showed an improvement in BROM values from 10 to 100 fold upon the addition of arbutin and BHT.

Lip Protection:

Full lips with an accentuated border have often been associated with beauty and youth. It has been suggested that this is because the lips occupy both sides of the face and, with the smile, constitute a major focal point of overall facial beauty. Currently the only treatment for lip rejuvenation caused by UV radiation, smoking and other environmental factors is the use of sunscreens. The effect of UV radiation is significantly more severe to the thin lip surface area, especially, if the lipstick, lip-gloss, lip or lip protectant product applied to the lip has chemical sunscreen includes. Sunscreen, especially on the lips only, protect three to five layers of keratinized cells that are continuously wiped and most likely swallowed when licking your lips. The sunscreens on the lip are subject to the same photolytic decomposition as the skin. The phototoxic effect of DNA begins a process of carcinogenesis which may lead to cancerous tumor growths. To help prevent the toxic cascade of events previously described for the skin the same series of antioxidants should protect the lip area by scavenging the damaging free radicals present due to UV radiation. Attached are a series of formulas that include arbutin and BHT to incorporate generically in all lipsticks to help prevent the formation of cancerous cells. Below are 3 non-limiting exemplary formulas for lip products applying the inventive technology disclosed herein.

Example 1—Lip Treatment—Formula JR-39-90E

| | |
|---|---|
| Carbowax 4000 (PEG-75) | 25.00 |
| Carbowax 8000 (PEG-180) | 25.00 |
| Carbowax 300 (PEG-6) | 29.70 |
| Benzyl Alcohol | 10.00 |
| Z-Cote (Zinc Oxide) | 10.00 |
| Arbutin | 00.20 |
| BHT | 00.10 |
| Total | 100.00 |

Example 2—Lip Treatment—Formula JR-39-88B

| | |
|---|---|
| Glycerin | 81.20 |
| Sodium Stearate | 08.50 |
| Benzyl Alcohol | 10.00 |
| Arbutin | 00.20 |
| BHT | 00.10 |
| Total | 100.00 |

Example 3—Lip Treatment—Formula JR-39-93B

| Ingredient | Amount |
|---|---|
| Petrolatum | 35.035 |
| C13-15 Alkane | 15.000 |
| Dimethicone | 02.000 |
| Polyglyceryl-3 behenate | 03.000 |
| BHT | 00.100 |
| Calcium Carbonate | 10.000 |
| Water | 06.565 |
| Glycerin | 22.000 |
| Phenoxyethanol | 01.000 |
| Potassium Sorbate | 00.100 |
| Arbutin | 00.200 |
| Total | 100.000 |

Table 10 below gives the composition of two other lipstick formulas with antioxidants and with and without the addition of Arbutin and BHT.

TABLE 10

| Lipstick Formula#1 with Anti-oxidants | |
|---|---|
| Active Ingredients: | |
| Octinoxate | 7.50% |
| Octisalate | 2.00% |
| Inactive Ingredients: | |
| *Ricinus Communis*, | 90.50% |
| | 23.60% |
| Candelilla Cera, | 4.50% |
| Octyldodecanol, | 20.75% |
| Ethylhexyl Methoxycinnamate | 5.00% |
| Vp/Hexadecene Copolymer, | 2.50% |
| Myristyl Lactate, | 2.00% |
| Caprylic/Capric Triglyceride, | 20.00% |
| Lanolin, | 2.00% |
| Ozokerite, | 1.50% |
| Castor Oil/Ipdi Copolymer, | 2.00% |
| *Crambe Abyssinica*, | <1% |
| Myristyl Myristate, | <1% |
| Ethylhexyl Salicylate, | <1% |
| Ethylhexyl Palmitate | <1% |
| Silica, Parfum, | <1% |
| Tocopherol, | <1% |
| Tribehenin, | <1% |
| Propylparaben, | <1% |
| Sorbitan Sesquioleate | <1% |
| Linalool, | <1% |
| *Copernicia Cerifera*, | <1% |
| Ascorbyl Palmitate, | <1% |
| Pentaerythrityl Tetraisostearate, | <1% |
| Sorbitan Isostearate, | <1% |
| Hydroxycitronellal, | <1% |
| Hexyl Cinnamal, | <1% |
| Aqua, | <1% |
| Retinyl Palmitate, | <1% |
| Bht, | <1% |
| Silica Dimethyl Silylate, | <1% |
| Cinnamyl Alcohol, | <1% |
| Geraniol, | <1% |
| Butylene Glycol, | <1% |
| Phenoxyethanol, | <1% |
| Palmitoyl Oligopeptide, | <1% |
| Sodium Chondroitin Sulfate, | <1% |
| Caprylyl Glycol, | <1% |
| Atelocollagen, | <1% |
| Sodium Hyaluronate, | <1% |
| Methylparaben, | <1% |
| Hexylene Glycol, | <1% |
| Ethylparaben, | <1% |
| Butylparaben, | <1% |
| Isobutylparaben, | <1% |
| Synthetic Fluorphlogopite, | <1% |
| Calcium Aluminum Borosilicate | <1% |
| Tin Oxide | <1% |
| May Contain: | |
| MICA, CI 77891, CI 77491, CI 77492, CI 77499, CI 15850, CI 19140, CI 45410, CI 15985, CI 17200, CI 42090, CI 75470. | |

BROM

| Sample [mg] | Time [s] | BROM [s/μg] |
|---|---|---|
| 16 | 0 | 0 |

Lipstick Formula #1 with Anti-Oxidants+1% Arbutin and 0.5% BHT
BROM

| Sample [mg] | Time [s] | BROM [s/μg] | Arbutin [mg] | BHT [mg] | Theoretical BROM [s/μg] | (BROM/TBROM − 1) * 100 [%] |
|---|---|---|---|---|---|---|
| 0.8339 | 375 | 0.45 | 0.00837 | 0.0039 | 0.607 | −25.976 |
| 1.1221 | 497 | 0.443 | 0.01126 | 0.00525 | 0.607 | −27.088 |
| Average: | | 0.45 | | | 0.61 | −26.5 |

For the above lipstick formulation with dozens of ingredients, a combination of 1% Arbutin to 0.5% BHT was added. The finished product BROM value of 0.45 secs/ug, which meets the criteria for finished products to have BROM values above 0.2 secs/ug, which the Applicant established when testing for phototoxicity. Testing cosmetic and pharmaceutical products for safety and the use of the BROM antioxidant value for the measurement of free radical scavenging capacity in the upper layers of the skin is a novel application for this antioxidant capacity assay.

All patents, test procedures, and other documents cited herein, including priority documents, are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

Other Exemplary Embodiments

In accordance with a first aspect of the disclosed embodiments, a method of screening antioxidants for protecting the skin from UV radiation is provided. The method includes applying the Briggs-Rauscher Oxidant Method (BROM) method to one or more antioxidants for predicting UV protective capacity to the epidermal layer of the skin.

In accordance with a first aspect of the disclosed embodiments, the method further includes optimizing the BROM method results to formulate antioxidant formulations for topically applied skin products requiring UV protection.

In accordance with a first sub-aspect of the disclosed embodiments, wherein the BROM value of the product is at least 0.2 sec/µg higher than the product without the optimized antioxidant formulation.

In accordance with a first aspect of the disclosed embodiments, wherein the topically applied skin products are chosen from sunscreens, lip sticks, lip balms, skin whiteners, cosmetic products, pharmaceutical products and dermatological products.

In accordance with a second aspect of the disclosed embodiments, an antioxidant formulation for use in sun screens, lip balms and other topically applied skin care products for protecting the skin from UV radiation is provided. The antioxidant formulation including a mixture of antioxidants in the skin care product including an effective amount of arbutin and BHT, wherein the ratio of arbutin to BHT in the skin care product ranges from 1:4 to 4:1, and wherein the measured BROM value of the antioxidant mixture is greater than the sum of the BROM values of the individual antioxidants in the mixture at the same concentration.

In accordance with a second aspect of the disclosed embodiments, the antioxidant formulation further including an effective amount of hydroquinone, resveratrol, atorvastatin, uric acid and combinations thereof.

In accordance with a second aspect of the disclosed embodiments, wherein the measured BROM value of the product is greater than or equal to 0.2 sec/µg.

In accordance with a second aspect of the disclosed embodiments, wherein the phototoxic potential as measured by the 3T3 Neutral Red Phototoxicity Test is at least 5% lower than a control carrier solution without the antioxidant formulation at a solution concentration range of from 0.0001-0.002%.

In accordance with a third aspect of the disclosed embodiments, an antioxidant formulation for use in sun screens, lip balms and other topically applied skin care products for protecting the skin from UV radiation is provided. The antioxidant formulation including a mixture of antioxidants in the skin care product including an effective amount of atorvastatin and BHT, wherein the ratio of atorvastatin to BHT in the skin care product ranges from 1:2 to 1:1, and wherein the measured BROM value of the antioxidant mixture is greater than the sum of the BROM values of the individual antioxidants in the mixture at the same concentration.

In accordance with a third aspect of the disclosed embodiments, the antioxidant formulation further including an effective amount of hydroquinone, resveratrol, arbutin, uric acid and combinations thereof.

In accordance with a third aspect of the disclosed embodiments, wherein the measured BROM value of the product is greater than or equal to 0.2 sec/µg.

In accordance with a first aspect of the disclosed embodiments, wherein the phototoxic potential as measured by the 3T3 Neutral Red Phototoxicity Test is at least 5% lower than a control carrier solution without the antioxidant formulation at a solution concentration range of from 0.0001-0.002%.

In accordance with a fourth aspect of the disclosed embodiments, an antioxidant formulation for use in sun screens, lip balms and other topically applied skin care products for protecting the skin from UV radiation is provided. The antioxidant formulation including a mixture of antioxidants in the skin care product including an effective amount of arbutin and hydroquinone, wherein the ratio of arbutin to hydroquinone in the skin care product ranges from 1:4 to 4:1, and wherein the measured BROM value of the antioxidant mixture is greater than the sum of the BROM values of the individual antioxidants in the mixture at the same concentration.

In accordance with a fourth aspect of the disclosed embodiments, the antioxidant formulation further including an effective amount of BHT, resveratrol, atorvastatin, uric acid and combinations thereof.

In accordance with a fourth aspect of the disclosed embodiments, wherein the measured BROM value of the product is greater than or equal to 0.2 sec/µg.

In accordance with a fourth aspect of the disclosed embodiments, wherein the phototoxic potential as measured by the 3T3 Neutral Red Phototoxicity Test is at least 5% lower than a control carrier solution without the antioxidant formulation at a solution concentration range of from 0.0001-0.002%.

In accordance with a fifth aspect of the disclosed embodiments, an antioxidant formulation for use in sun screens, lip balms and other topically applied skin care products for protecting the skin from UV radiation is provided. The antioxidant formulation including a mixture of antioxidants in the skin care product including an effective amount of hydroquinone and BHT, wherein the ratio of hydroquinone to BHT in the skin care product ranges from 1:4 to 4:1, and wherein the measured BROM value of the antioxidant mixture is greater than the sum of the BROM values of the individual antioxidants in the mixture at the same concentration.

In accordance with a fifth aspect of the disclosed embodiments, the antioxidant formulation further including an effective amount of arbutin, resveratrol, atorvastatin, uric acid, and combinations thereof.

In accordance with a fifth aspect of the disclosed embodiments, wherein the measured BROM value of the product is greater than or equal to 0.2 sec/µg.

In accordance with a fifth aspect of the disclosed embodiments, wherein the phototoxic potential as measured by the 3T3 Neutral Red Phototoxicity Test is at least 5% lower than a control carrier solution without the antioxidant formulation at a solution concentration range of from 0.0001-0.002%.

In accordance with a sixth aspect of the disclosed embodiments, an antioxidant formulation for use in sun screens, lip balms and other topically applied skin care products for protecting the skin from UV radiation is provided. The antioxidant formulation includes a mixture of antioxidants in the skin care product including an effective amount of atorvastatin and uric acid, wherein the ratio of atorvastatin to uric acid in the skin care product ranges from 0.5:1 to 2:1, and wherein the measured BROM value of the antioxidant mixture is greater than the sum of the BROM values of the individual antioxidants in the mixture at the same concentration.

In accordance with a sixth aspect of the disclosed embodiments, the antioxidant formulation further including an effective amount of hydroquinone, resveratrol, arbutin, BHT, uric acid and combinations thereof.

In accordance with a sixth aspect of the disclosed embodiments, wherein the measured BROM value of the product is greater than or equal to 0.2 sec/µg.

In accordance with a sixth aspect of the disclosed embodiments, wherein the phototoxic potential as measured by the 3T3 Neutral Red Phototoxicity Test is at least 5% lower than a control carrier solution without the antioxidant formulation at a solution concentration range of from 0.0001-0.002%.

In accordance with a seventh aspect of the disclosed embodiments, an antioxidant formulation for use in sun screens, lip balms and other topically applied skin care products for protecting the skin from UV radiation is provided. The antioxidant formulation includes a mixture of antioxidants in the skin care product including an effective amount of uric acid, atorvastatin and BHT, wherein the ratio of uric acid, atorvastatin and BHT in the skin care product ranges from 1:1:4 to 4:1:1, and wherein the measured BROM value of the antioxidant mixture is greater than the sum of the BROM values of the individual antioxidants in the mixture at the same concentration.

In accordance with a seventh aspect of the disclosed embodiments, the antioxidant formulation further including an effective amount of hydroquinone, resveratrol, arbutin, and combinations thereof.

In accordance with a seventh aspect of the disclosed embodiments, wherein the measured BROM value of the product is greater than or equal to 0.2 sec/µg.

In accordance with a seventh aspect of the disclosed embodiments, wherein the phototoxic potential as measured by the 3T3 Neutral Red Phototoxicity Test is at least 5% lower than a control carrier solution without the antioxidant formulation at a solution concentration range of from 0.0001-0.002%.

In accordance with an eighth aspect of the disclosed embodiments, an antioxidant formulation for use in sun screens, lip balms and other topically applied skin care products for protecting the skin from UV radiation is provided. The antioxidant formulation includes a mixture of antioxidants in the skin care product including an effective amount of arbutin and resveratrol, wherein the ratio of arbutin to resveratrol in the skin care product ranges from 1:4 to 4:1, and wherein the measured BROM value of the antioxidant mixture is greater than the sum of the BROM values of the individual antioxidants in the mixture at the same concentration.

In accordance with an eighth aspect of the disclosed embodiments, the antioxidant formulation further including an effective amount of hydroquinone, BHT, atorvastatin, uric acid and combinations thereof.

In accordance with an eighth aspect of the disclosed embodiments, wherein the measured BROM value of the product is greater than or equal to 0.2 sec/µg.

In accordance with an eighth aspect of the disclosed embodiments, wherein the phototoxic potential as measured by the 3T3 Neutral Red Phototoxicity Test is at least 5% lower than a control carrier solution without the antioxidant formulation at a solution concentration range of from 0.0001-0.002%.

In accordance with an ninth aspect of the disclosed embodiments, an antioxidant formulation for use in sun screens, lip balms and other topically applied skin care products for protecting the skin from UV radiation is provided. The antioxidant formulation includes a mixture of antioxidants in the skin care product including an effective amount of BHT and resveratrol, wherein the ratio of BHT to resveratrol in the skin care product ranges from 1:4 to 4:1, and wherein the measured BROM value of the antioxidant mixture is greater than the sum of the BROM values of the individual antioxidants in the mixture at the same concentration.

In accordance with an ninth aspect of the disclosed embodiments, the antioxidant formulation further including an effective amount of hydroquinone, arbutin, atorvastatin, uric acid and combinations thereof.

In accordance with an ninth aspect of the disclosed embodiments, wherein the measured BROM value of the product is greater than or equal to 0.2 sec/µg.

In accordance with an ninth aspect of the disclosed embodiments, wherein the phototoxic potential as measured by the 3T3 Neutral Red Phototoxicity Test is at least 5% lower than a control carrier solution without the antioxidant formulation at a solution concentration range of from 0.0001-0.002%.

In accordance with a tenth aspect of the disclosed embodiments, an antioxidant formulation for use in sun screens, lip balms and other topically applied skin care products for protecting the skin from UV radiation is provided. The antioxidant formulation includes a mixture of antioxidants in the skin care product including an effective amount of atorvastatin and hydroquinone, wherein the ratio of atorvastatin to hydroquinone in the skin care product ranges from 1:4 to 4:1, and wherein the measured BROM value of the antioxidant mixture is greater than the sum of the BROM values of the individual antioxidants in the mixture at the same concentration.

In accordance with a tenth aspect of the disclosed embodiments, the antioxidant formulation further including an effective amount of BHT, resveratrol, arbutin, uric acid and combinations thereof.

In accordance with a tenth aspect of the disclosed embodiments, wherein the measured BROM value of the product is greater than or equal to 0.2 sec/µg.

In accordance with a tenth aspect of the disclosed embodiments, wherein the phototoxic potential as measured by the 3T3 Neutral Red Phototoxicity Test is at least 5% lower than a control carrier solution without the antioxidant formulation at a solution concentration range of from 0.0001-0.002%.

In accordance with an eleventh aspect of the disclosed embodiments, an antioxidant formulation for use in sun screens, lip balms and other topically applied skin care products for protecting the skin from UV radiation is provided. The antioxidant formulation includes a mixture of antioxidants in the skin care product including an effective amount of arbutin, hydroquinone and BHT, wherein the ratio of arbutin, hydroquinone and BHT in the skin care product ranges from 2:1:1 to 2:1:4, and wherein the measured BROM value of the antioxidant mixture is greater than the sum of the BROM values of the individual antioxidants in the mixture at the same concentration.

In accordance with an eleventh aspect of the disclosed embodiments, the antioxidant formulation further including an effective amount of atorvastatin, resveratrol, uric acid and combinations thereof.

In accordance with an eleventh aspect of the disclosed embodiments, wherein the measured BROM value of the product is greater than or equal to 0.2 sec/μg.

In accordance with an eleventh aspect of the disclosed embodiments, wherein the phototoxic potential as measured by the 3T3 Neutral Red Phototoxicity Test is at least 5% lower than a control carrier solution without the antioxidant formulation at a solution concentration range of from 0.0001-0.002%.

In accordance with a twelfth aspect of the disclosed embodiments, an antioxidant formulation for use in sun screens, lip balms and other topically applied skin care products for protecting the skin from UV radiation is provided. The antioxidant formulation includes a mixture of antioxidants in the skin care product including an effective amount of arbutin, BHT and resveratrol, wherein the ratio of arbutin, BHT and resveratrol in the skin care product ranges from 1:1:1 to 2:1:2, and wherein the measured BROM value of the antioxidant mixture is greater than the sum of the BROM values of the individual antioxidants in the mixture at the same concentration.

In accordance with a twelfth aspect of the disclosed embodiments, further including an effective amount of atorvastatin, hydroquinone, uric acid and combinations thereof.

In accordance with a twelfth aspect of the disclosed embodiments, wherein the measured BROM value of the product is greater than or equal to 0.2 sec/μg.

In accordance with a twelfth aspect of the disclosed embodiments, wherein the phototoxic potential as measured by the 3T3 Neutral Red Phototoxicity Test is at least 5% lower than a control carrier solution without the antioxidant formulation at a solution concentration range of from 0.0001-0.002%.

What is claimed is:

1. An antioxidant formulation for use in sun screens, lip balms and other topically applied skin care products for protecting the skin from UV radiation comprising: a mixture of antioxidants in the skin care product including an effective amount of atorvastatin and butylated hydroxytoluene (BHT), wherein the ratio of atorvastatin to BHT in the skin care product ranges from 1:2 to 1:1, and wherein the measured BROM value of the antioxidant mixture is greater than the sum of the BROM values of the individual antioxidants in the mixture at the same concentration.

2. The antioxidant formulation of claim 1, further including an effective amount of hydroquinone, resveratrol, arbutin, uric acid and combinations thereof.

3. The antioxidant formulation of claim 1, wherein the measured BROM value of the product is greater than or equal to 0.2 sec/μg.

4. The antioxidant formulation of claim 1, wherein the phototoxic potential as measured by the 3T3 Neutral Red Phototoxicity Test is at least 5% lower than a control carrier solution without the antioxidant formulation at a solution concentration range of from 0.0001-0.002%.

5. An antioxidant formulation for use in sun screens, lip balms and other topically applied skin care products for protecting the skin from UV radiation comprising: a mixture of antioxidants in the skin care product including an effective amount of uric acid, atorvastatin and BHT, wherein the ratio of uric acid, atorvastatin and BHT in the skin care product ranges from 1:1:2 to 2:1:1, and wherein the measured BROM value of the antioxidant mixture is greater than the sum of the BROM values of the individual antioxidants in the mixture at the same concentration.

6. The antioxidant formulation of claim 5, further including an effective amount of hydroquinone, resveratrol, arbutin, and combinations thereof.

7. The antioxidant formulation of claim 5, wherein the measured BROM value of the product is greater than or equal to 0.2 sec/μg.

8. The antioxidant formulation of claim 5, wherein the phototoxic potential as measured by the 3T3 Neutral Red Phototoxicity Test is at least 5% lower than a control carrier solution without the antioxidant formulation at a solution concentration range of from 0.0001-0.002%.

* * * * *